United States Patent [19]

Cheng

[11] Patent Number: 5,199,452
[45] Date of Patent: Apr. 6, 1993

[54] DENTAL FLOSSING ARRANGEMENT AND METHOD

[76] Inventor: Peter S. C. Cheng, 5 Ross Street, Toronto, Ontario, Canada, M5T 1Z8

[21] Appl. No.: 901,180

[22] Filed: Jun. 19, 1992

[51] Int. Cl.⁵ .............................................. A61C 15/00
[52] U.S. Cl. .................... 132/325; 132/323; 132/324
[58] Field of Search ............... 132/323, 324, 325, 326, 132/327

[56] References Cited

U.S. PATENT DOCUMENTS

| | | | |
|---|---|---|---|
| 2,381,530 | 8/1945 | Dembenski | 132/325 |
| 3,592,203 | 7/1971 | Johnson | 132/323 |
| 3,696,821 | 10/1972 | Adams, IV | 132/324 |
| 3,746,017 | 7/1973 | Casselman | 132/325 |
| 3,799,177 | 3/1974 | Bragg | 132/326 |
| 3,901,251 | 8/1975 | Johnston | 132/326 |
| 4,050,470 | 9/1977 | Miller | 132/323 |
| 4,254,786 | 3/1981 | Won | 132/325 |
| 5,085,236 | 2/1992 | Odneal et al. | 132/325 |

*Primary Examiner*—Gene Mancene
*Assistant Examiner*—Frank A. LaViola
*Attorney, Agent, or Firm*—Kirschstein, Ottinger, Israel & Schiffmiller

[57] ABSTRACT

A supply of dental floss is wound on a supply reel turnably mounted in one housing, while another housing mounts a take-up reel for receiving spent floss. The housings are held in opposite hands of a user with the floss extending therebetween. During flossing, a dispensed length of floss is held taut by fixedly anchoring the dispensed floss within the housings. After flossing, the dispensed floss is wound on the take-up reel for easy disposal.

12 Claims, 3 Drawing Sheets

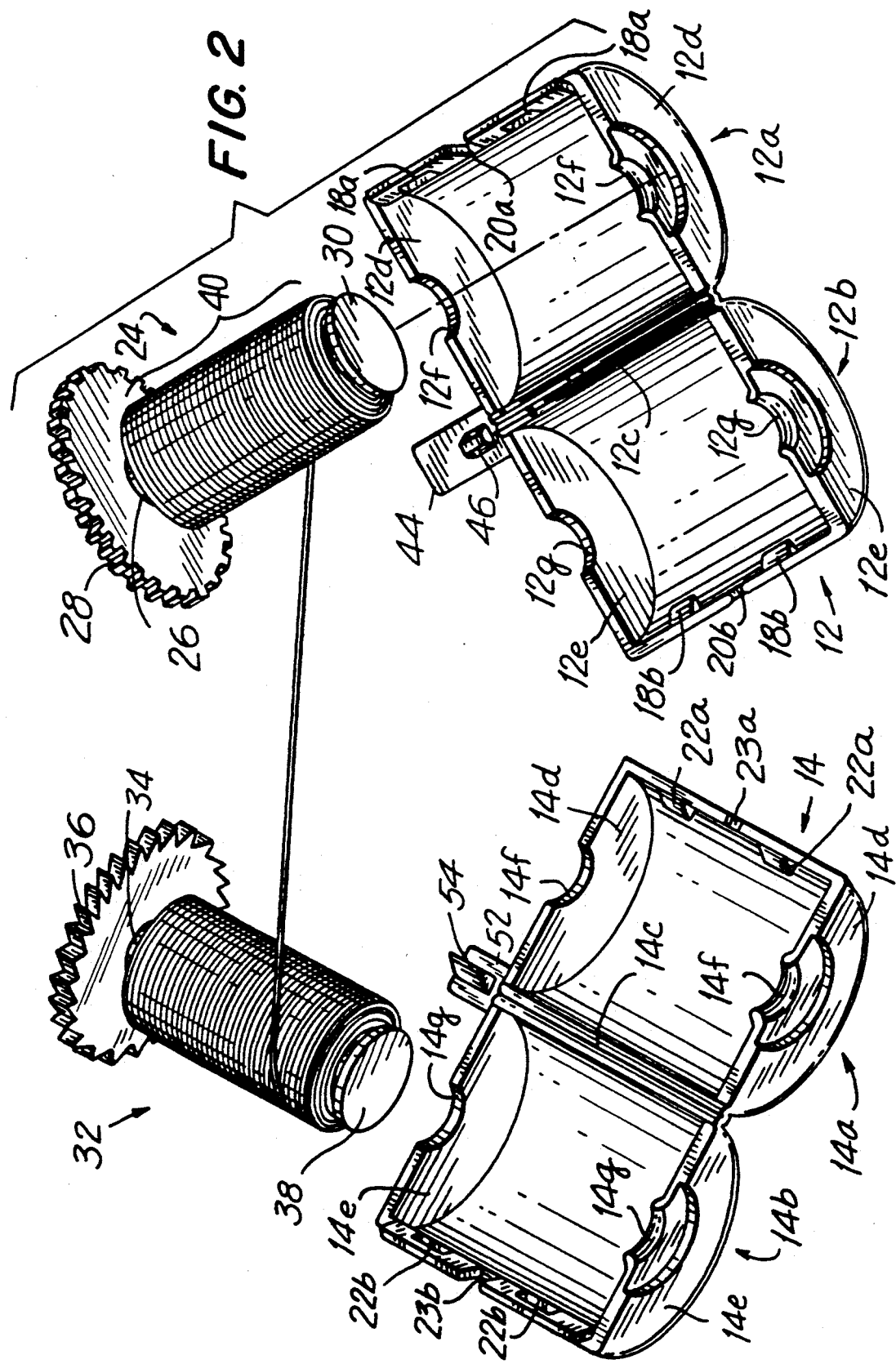

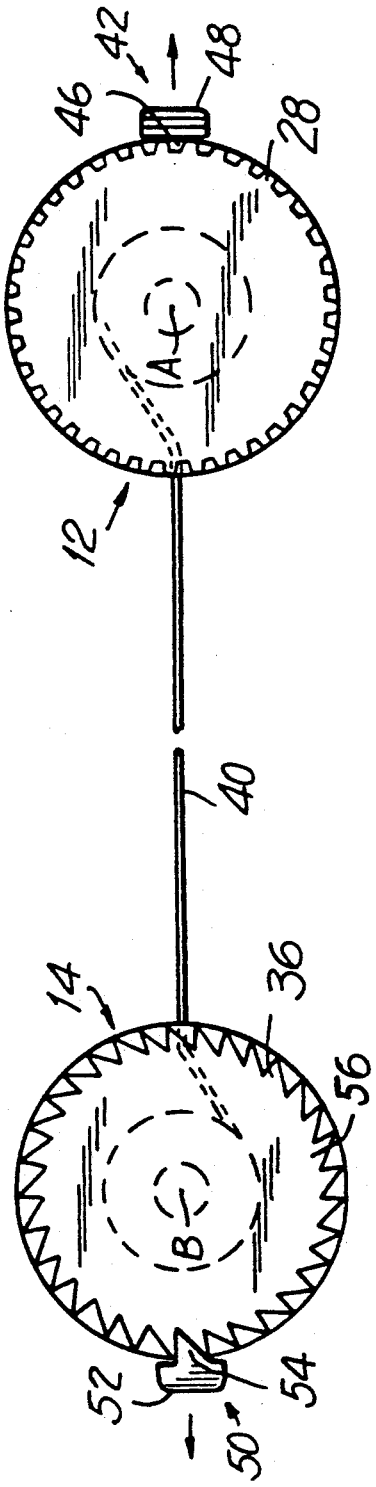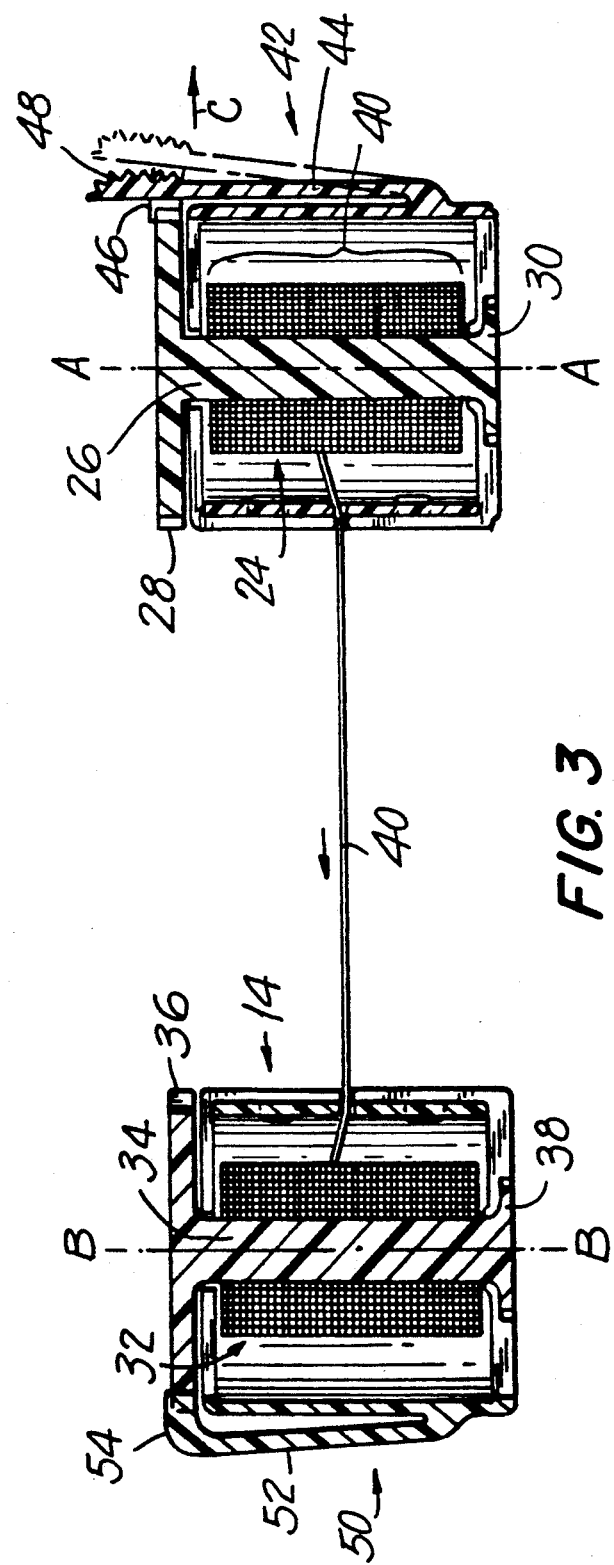

DENTAL FLOSSING ARRANGEMENT AND METHOD

BACKGROUND OF THE INVENTION

1. Field of the Invention

This invention generally relates to an arrangement for and method of flossing teeth and, more particularly, to a sanitary floss dispensing and manipulation system.

2. Description of Related Art

Proper dental hygiene requires flossing between adjacent teeth to clear food deposits and naturally occurring bacteria acting thereon. Typically, a length of floss is wound tightly about the forefingers of each hand, and the span of floss held between the forefingers is inserted into the interdental spaces. This flossing technique tends to cut off circulation and causes discomfort in the fingertips.

Various floss holders of the type exemplified by U.S. Pat. Nos. 2,381,530; 3,340,881; 3,901,251 and 5,085,236 have been designed to address these problems. However, the known holders are fairly cumbersome and too big to manipulate easily in one's mouth, especially when access to difficult-to-reach rear molars is desired.

SUMMARY OF THE INVENTION

1. Objects of the Invention

It is a general object of this invention to provide a compact, lightweight dental flossing arrangement which fits easily into a user's mouth.

It is another object of this invention to provide such an arrangement which can be used in comfort without cutting off the circulation in one's fingers.

Another object of this invention is to hygienically dispense fresh floss and to discard spent floss.

2. Features of the Invention

In keeping with these objects, and others which will become apparent hereinafter, one feature of this invention resides, briefly stated, in a dental flossing arrangement comprising a pair of discrete housings configured to be held in opposite hands of a user. A supply reel is mounted for turning movement on one of the housings. A take-up reel is mounted for turning movement on the other of the housings. A supply of dental floss wound on the supply reel extends therefrom between the housings to the take-up reel.

The arrangement comprises first releasable locking means on the supply reel housing for preventing movement of the supply reel in a locked state, and for selectively releasing the supply reel to dispense a length of floss. Second releasable locking means are provided on the take-up housing for preventing movement of the take-up reel in a locked state. In the locked states of the supply and take-up reels, the dispensed length of floss is held taut between the housings during flossing. After flossing, the take-up reel is released by wind-up means in order to wind the dispensed length of floss thereon.

In a preferred embodiment, each housing has a pair of hinged parts movable between open and closed positions, and an opening through which the floss extends. The floss has opposite ends operatively connected to the reels. The floss and the reels are removably mounted as a unitary assembly on the housings in their open positions. This provides for convenient installation of fresh floss and for convenient and sanitary discarding of spent floss.

The first locking means includes a resilient cantilever-type spring of one piece with the supply housing. A lock is mounted on the spring and is normally biased into locking engagement with a toothed wheel located exteriorly of the supply housing. A release on the spring selectively releases the lock from such locking engagement.

The second locking means includes a resilient spring of one piece with the take-up housing, and a catch on the spring and normally biased into ratcheting engagement with a ratchet wheel located exteriorly of the take-up housing. The ratchet wheel has teeth sloped along a circumferential direction, thereby permitting forward movement and preventing backward movement in the locked state of the take-up reel. The wind-up means includes a grip on the ratchet wheel for moving the same along the forward direction past the catch.

In use of the method of dental flossing according to this invention, a supply of dental floss is initially wound on the supply reel, and a leading end of the floss is fed to the take-up reel. The supply and take-up reels are respectively mounted for turning movement on the two housings which, as previously noted, are held in opposite hands. The supply and take-up reels are: initially prevented from turning movement in respective locked states.

In order to floss one's teeth, the user selectively releases the supply reel and pulls the housings apart to dispense a length of floss from the supply reel. Thereupon, the dispensed length of floss is held taut between the housings while flossing occurs. After flossing, the take-up reel is turned and the spent floss is wound on the take-up reel. Once all the floss has been exhausted from the supply reel, both housings can be opened and the unitary assembly, consisting of the two take-up reels and the floss supply, can be conveniently discarded.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is an exploded, perspective view showing how the arrangement of FIG. 1 is pre-loaded with dental floss;

FIG. 3 is a sectional view through the arrangement of FIG. 1;

FIG. 4 is a top plan view of part of the arrangement of FIG. 3; and

FIG. 5 is a top plan view of another part of the arrangement of FIG. 3.

DETAILED DESCRIPTION OF THE PREFERRED EMBODIMENT

Figure 1:
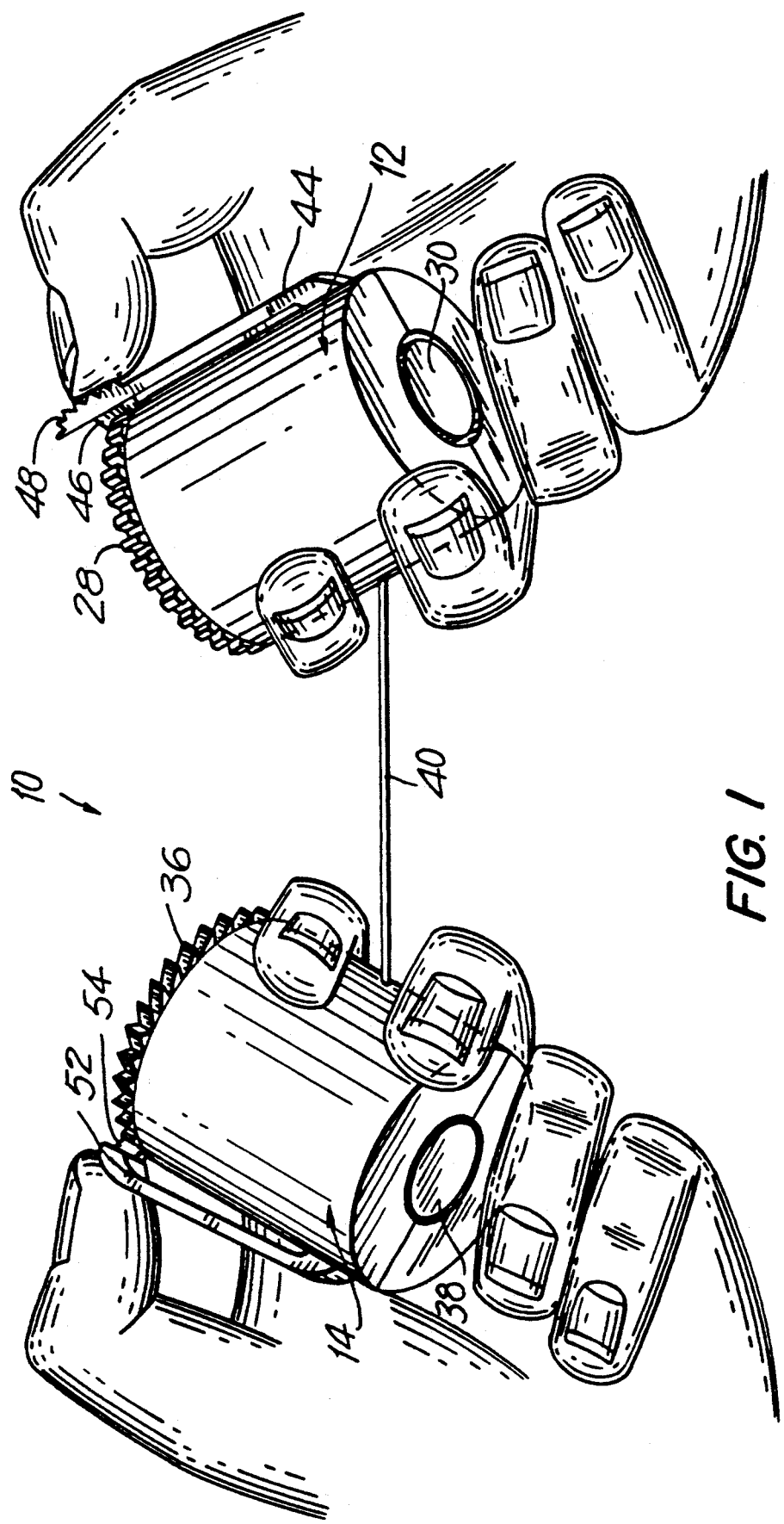
FIG. 1 is a perspective view of a dental flossing arrangement in use according to the method of this invention.

Referring now to the drawings, reference numeral 10 generally identifies a dental flossing arrangement comprising a supply housing 12 and a take-up housing 14, each of cylindrical configuration and being sized to fit within the closed opposite hands of a user during flossing (see FIG. 1). Each housing is constituted of a synthetic plastic material, and has a pair of semi-cylindrical sections 12a, 12b and 14a, 14b, respectively hinged at and along integral living hinges 12c, 14c for movement between open (FIG. 2) and closed (FIG. 1) positions.

Each housing section 12a, 12b has opposite, mutually parallel, semi-circular, generally planar end walls 12d, 12e, each formed with a semi-circular aperture 12f, 12g. Each housing section 14a, 14b has opposite, mutually parallel, semi-circular, generally planar end walls 14d, 14e, each with a semi-circular aperture 14f, 14g.

Each housing section 12a, 12b has snap locks 18a, 18b which engage each other with snap action in the closed position. Each lock 18a, 18b has a semi-circular hole 20a, 20b. Each housing section 14a, 14b has snap locks 22a, 22b which engage each other with snap action in the closed position. Each lock 22a, 22b has a semi-circular hole 23a, 23b.

A supply reel 24 is mounted for turning movement on the supply housing 12. Reel 24 includes a shaft 26 extending along a turning axis A—A, a gear wheel 28 fixed at one end of the shaft 26, and a flange 30 at the opposite end of the shaft 26. Gear wheel 28 has a plurality of triangular, radially-symmetrical teeth equiangularly arranged about the turning axis A—A.

A take-up reel 32 is mounted for turning movement on the take-up housing 14. Reel 32 includes a shaft 34 extending along a turning axis B—B, a ratchet gear wheel 36 fixed at one end of the shaft 34, and a flange 38 at the opposite end of the shaft 34. Ratchet wheel 36 has a plurality of asymmetrical ratchet teeth which are sloped in one circumferential direction, i.e. counter-clockwise, in FIG. 5, and equiangularly arranged about the turning axis B—B.

A supply of dental floss 40 is initially wound in a predetermined length, e.g. 10 meters, on the supply reel 24 and extends therefrom to the take-up reel 32. Reels 24, 32, together with the floss 40, are mounted as a unitary assembly on the housings 12, 14 in their open positions (FIG. 2). The reels are positioned such that the flanges 30, 38, as well as the wheels 28, 36, are all located exteriorly of their respective housings. Reel shafts 26, 34 are supportably journaled in the apertures 12f, 12g and 14f, 14g, respectively. The floss 40 is threaded through the holes 20a, 20b and 23a, 23b, and spans the distance between the housings.

A first releasable locking means 42 is provided on supply housing 12 for preventing movement of the supply reel 24 in a locked state, and for selectively releasing the supply reel to dispense a length of floss therefrom. Means 42 includes a resilient cantilever spring 44 of one piece with the housing 12, and a lock 46 adjacent the free end of the spring. Spring 44, due to its inherent resilience, normally biases the lock 46 into locking, meshing engagement with the teeth of the gear wheel 28. Once so locked, the gear wheel 28 cannot be turned in either circumferential direction about the axis A—A.

A release 48 extending away from the lock 46 at the free end of the spring 44 is a finger grip. When pulled in the direction of arrow C in FIG. 3 against the restoring force of the spring 44, the lock 46 is disengaged from the gear wheel 28, thereby freeing the supply reel 24 for movement. By letting go of the release 48, the spring 44 returns, due to its inherent resilience, and biases the lock 46 into engagement with the gear wheel 28.

A second releasable locking means 50 is provided on the take-up housing 14 for preventing movement of the take-up reel 32 in a locked state. Means 50 includes a resilient cantilever spring 52 of one piece with the housing 14, and a catch 54 at the free end of spring 52. Spring 52 normally biases the catch 54, due to its inherent resilience, into ratcheting engagement with the teeth on ratchet wheel 36. Once so engaged, the ratchet gear wheel 36 cannot be turned in the aforementioned circumferential direction, thereby defining the locked state for the take-up reel.

In use, after the reels have been loaded into their respective housings with the floss spanning the distance therebetween, a user initially actuates the release 48, preferably with his or her thumb, and pushes the release 48 in the direction of the arrow C. Thereupon, the user pulls the housings apart to dispense a length of floss, e.g. 15-30 cm, from the supply reel. During this pulling apart step, the supply reel 24 is in an unlocked state, whereas the take-up reel 32 is in a locked state. Upon removing the pressure exerted on the release 48, the supply reel 24 is once again in the locked state where it remains during flossing. Discomfort to the user's fingers is reliably prevented because the floss is not wound tightly around the user's fingers, but, instead, opposite ends of the dispensed length of floss is securely anchored within each housing.

Once flossing is completed, a wind-up means, e.g. a grip 56 on the ratchet wheel 36, is operative for winding the dispensed length of spent floss on the take-up reel 32. The user need only turn the ratchet wheel 36 with his or her thumb in a clockwise direction, thereby allowing the catch 54 to ride along the sloped teeth of the ratchet wheel 36. The ratchet wheel, of course, is prevented by the catch 54 from being rotated in the counter-clockwise direction, thereby assuring that the user will not floss his or her teeth with spent floss.

After repeated uses, all of the floss initially wound on the supply reel 24 will be transferred to the take-up reel 32, at which time, both reels and the spent floss may be removed from their respective housings, thereby readying the arrangement to be loaded with a fresh supply of reels and floss.

Other features of the dental flossing arrangement include providing a see-through window on the supply housing to enable the user to visually gauge the amount of floss remaining on the supply reel, color and/or indicia codings on the housings so that the user can easily distinguish between them, and a kit with multiple refills of reels and floss. Thus, the kit would include a single pair of housings and multiple sets of reels and floss, each set being disposable.

It will be understood that each of the elements described above, or two or more together, also may find a useful application in other types of constructions differing from the types described above.

While the invention has been illustrated and described as embodied in a dental flossing arrangement and method, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A dental flossing arrangement, comprising:
   (a) a pair of discrete housing configured to be held in opposite hands of a user;
   (b) a supply reel mounted for turning movement on one of the housings;
   (c) a take-up reel mounted for turning movement on the other of the housings;
   (d) a supply of dental floss wound on the supply reel and extending from the supply reel between the housings to the take-up reel;
   (e) first releasable locking means including a first resilient spring on said one housing for normally preventing movement of the supply reel in a locked state due to the inherent resilience of the first spring, and for selectively releasing the supply reel to dispense a length of floss from the supply reel;
   (f) second releasable locking means including a second resilient spring on said other housing for normally preventing movement of the take-up reel in a locked state due to the inherent resilience of the second spring to thereby hold the dispensed length of floss taut between the housings in the locked states of the supply and take-up reels during flossing; and
   (g) wind-up means on the take-up reel for releasing the take-up reel to wind the dispensed length of floss on the take-up reel after flossing.

2. The arrangement according to claim 1, wherein each housing has housing parts movable between open and closed positions, and an opening through which the floss extends.

3. The arrangement according to claim 2, wherein the housing parts of each housing are hinged.

4. The arrangement according to claim 2, wherein the floss has opposite ends operatively connected to the reels; and wherein the floss and the reels are removably mounted, as a unitary assembly, on the housings in their open positions.

5. The arrangement according to claim 1, wherein each reel has an elongated shaft on which the floss is wound, and a toothed wheel at one end of a respective shaft and located exteriorly of a respective housing.

6. The arrangement according to claim 5, wherein the first releasable locking means includes said first resilient spring of one piece with said one housing, a lock on the first spring and biased into locking engagement with the toothed wheel exteriorly of said one housing, and a release on the first spring for selectively releasing the lock from said locking engagement.

7. The arrangement according to claim 5, wherein the toothed wheel exteriorly of said other housing is a ratchet wheel having teeth sloped along a circumferential direction; and wherein the second releasable locking means includes said second resilient spring of one piece with said other housing, and a catch on the second spring and biased into ratcheting engagement with the ratchet wheel.

8. The arrangement according to claim 7, wherein the wind-up means includes a grip on the ratchet wheel for moving the ratchet wheel along a forward direction past the catch.

9. A method of dental flossing, comprising the steps of:
   (a) winding a supply of dental floss on a supply reel, and feeding a leading end of the floss to a take-up reel;
   (b) mounting the supply reel for turning movement on one housing;
   (c) mounting the take-up reel for turning movement on another housing;
   (d) holding one housing in one hand of a user, and holding the other housing in the opposite hand of the user;
   (e) preventing turning movement of the supply reel in a locked state;
   (f) preventing turning movement of the take-up reel in a locked state;
   (g) selectively releasing the supply reel and pulling the housings apart to dispense a length of floss from the supply reel;
   (h) holding the dispensed length of floss taut between the housings in their locked states;
   (i) flossing teeth while holding taut the dispensed length of floss; and
   (j) turning the take-up reel, and winding the dispensed length of floss on the take-up reel after flossing.

10. The method according to claim 9, wherein the mounting steps are performed by opening both housings, and by placing both reels and the floss therebetween, as a unitary assembly, on the opened housings.

11. The method according to claim 9, wherein the releasing step is performed by manually moving a lock out of locking engagement with said one housing.

12. The method according to claim 9, wherein the turning step is performed by manually moving the take-up reel.

* * * * *